(12) United States Patent
Winkler et al.

(10) Patent No.: US 7,494,457 B2
(45) Date of Patent: Feb. 24, 2009

(54) BRACHYTHERAPY APPARATUS AND METHOD FOR TREATING A TARGET TISSUE THROUGH AN EXTERNAL SURFACE OF THE TISSUE

(75) Inventors: Rance A. Winkler, Atlanta, GA (US); Bartolome J. Salazar, Alpharetta, GA (US); Timothy J. Patrick, Alpharetta, GA (US); James B. Stubbs, Alpharetta, GA (US)

(73) Assignee: CYTYC Corporation, Marlborough, MA (US)

( * ) Notice: Subject to any disclaimer, the term of this patent is extended or adjusted under 35 U.S.C. 154(b) by 756 days.

(21) Appl. No.: 10/704,344

(22) Filed: Nov. 7, 2003

(65) Prior Publication Data

US 2005/0101825 A1  May 12, 2005

(51) Int. Cl.
*A61M 36/00* (2006.01)
(52) U.S. Cl. .......................................................... 600/7
(58) Field of Classification Search ................. 600/1–8; 606/192; 250/519.1; 604/103.1, 103.11, 604/103.07
See application file for complete search history.

(56) References Cited

U.S. PATENT DOCUMENTS

| | | | | |
|---|---|---|---|---|
| 3,324,847 A | 6/1967 | Zoumboulis | .................. | 128/1.2 |
| 3,872,856 A | 3/1975 | Clayton | ...................... | 128/1.2 |
| 4,417,576 A | 11/1983 | Baran | ..................... | 128/207.15 |
| 4,706,652 A | 11/1987 | Horowitz | .................... | 128/1.2 |
| 4,754,745 A | 7/1988 | Horowitz | .................... | 128/1.2 |
| 4,763,642 A | 8/1988 | Horowitz | .................... | 128/1.2 |
| 4,821,725 A | 4/1989 | Azam et al. | ............. | 128/420 A |
| 4,867,741 A | 9/1989 | Portnoy | ........................ | 604/10 |
| 5,030,195 A | 7/1991 | Nardi | ............................ | 600/7 |
| 5,084,001 A | 1/1992 | Van't Hooft et al. | ........... | 600/3 |
| 5,084,015 A | 1/1992 | Moriuchi | ..................... | 604/96 |
| 5,106,360 A | 4/1992 | Ishiwara et al. | ................ | 600/2 |

(Continued)

FOREIGN PATENT DOCUMENTS

EP   0340881   11/1989

(Continued)

OTHER PUBLICATIONS

Ashpole, R.D. et al., "A New Technique of Brachytherapy for Malignant Gliomas with Caesium-137: A New Method Utilizing a Remote Afterloading System," Clinical Oncology, vol. 2, 333-7 (1990).

(Continued)

*Primary Examiner*—Charles A. Marmor, II
*Assistant Examiner*—Christine D Hopkins
(74) *Attorney, Agent, or Firm*—Heather Larson (57) ABSTRACT

A brachytherapy device is provided for treating a target tissue through an external surface area of the target tissue. The device includes an insertion member having a proximal portion, a distal portion, and at least one lumen extending therethrough. A fluid retaining member is mated to the distal portion of the insertion member and has a first surface shaped to conform to a predetermined external surface area of a tissue to be treated, and a cavity formed therein in fluid communication with the at least one lumen in the insertion member. A plurality of anchor members can be distributed about a periphery of the first surface to anchor the first surface to an external surface area of a tissue to be treated.

7 Claims, 4 Drawing Sheets

U.S. PATENT DOCUMENTS

| | | | |
|---|---|---|---|
| 5,112,303 A | 5/1992 | Pudenz et al. ................. 604/49 |
| 5,152,747 A | 10/1992 | Olivier ........................ 604/93 |
| 5,236,410 A | 8/1993 | Granov et al. ................. 600/12 |
| 5,429,582 A | 7/1995 | Williams ........................ 600/2 |
| 5,484,384 A | 1/1996 | Fearnot ........................ 600/3 |
| 5,503,613 A | 4/1996 | Weinberger ................... 600/3 |
| 5,566,221 A | 10/1996 | Smith et al. ................. 378/145 |
| 5,611,767 A | 3/1997 | Williams ........................ 600/2 |
| 5,662,580 A | 9/1997 | Bradshaw et al. .............. 600/3 |
| 5,707,332 A | 1/1998 | Weinberger ................... 600/3 |
| 5,713,828 A | 2/1998 | Coniglione .................... 600/7 |
| 5,720,717 A | 2/1998 | D'Andrea ..................... 604/21 |
| 5,764,723 A | 6/1998 | Weinberger et al. ........... 378/65 |
| 5,782,742 A | 7/1998 | Crocker et al. ................. 600/3 |
| 5,785,688 A | 7/1998 | Joshi et al. .................. 604/141 |
| 5,795,325 A * | 8/1998 | Valley et al. ................ 604/509 |
| 5,931,774 A | 8/1999 | Williams et al. |
| 5,993,374 A | 11/1999 | Kick .............................. 600/8 |
| 6,036,631 A | 3/2000 | McGrath et al. ............... 600/3 |
| 6,048,299 A | 4/2000 | Hoffmann ..................... 600/3 |
| 6,083,148 A | 7/2000 | Williams |
| 6,120,523 A | 9/2000 | Crocker et al. .............. 606/192 |
| 6,149,574 A | 11/2000 | Trauthen et al. ............... 600/3 |
| 6,176,821 B1 | 1/2001 | Crocker et al. ................. 600/3 |
| 6,261,320 B1 | 7/2001 | Tam et al. ................... 623/1.15 |
| 6,287,249 B1 | 9/2001 | Tam et al. ...................... 600/3 |
| 6,413,204 B1 | 7/2002 | Winkler et al. |
| 6,419,692 B1 | 7/2002 | Yang et al. ................. 623/1.15 |
| 6,458,069 B1 | 10/2002 | Tam et al. ...................... 600/3 |
| 6,471,630 B1 | 10/2002 | Sioshansi et al. ............... 600/1 |
| 6,482,142 B1 | 11/2002 | Winkler et al. |
| 6,487,438 B1 | 11/2002 | Widmark et al. ............ 600/431 |
| 2002/0022799 A1* | 2/2002 | Apple ..................... 604/96.01 |
| 2003/0028097 A1 | 2/2003 | D'Amico et al. ............ 600/427 |
| 2003/0032851 A1 | 2/2003 | Apple et al. |
| 2003/0114878 A1 | 6/2003 | Diederich et al. ........... 606/192 |

FOREIGN PATENT DOCUMENTS

| | | |
|---|---|---|
| EP | 0 085 957 A2 | 7/1998 |
| EP | 0867200 | 9/1998 |
| GB | 2105201 | 3/1983 |
| WO | 9210932 | 7/1992 |
| WO | 9309724 | 5/1993 |
| WO | 9719723 | 6/1997 |
| WO | 9812979 | 4/1998 |
| WO | 9911325 | 3/1999 |
| WO | 9933515 | 7/1999 |
| WO | 9942163 | 8/1999 |

OTHER PUBLICATIONS

A. Bex et al., "A System For Focal Intracavitary Irradiation Of Bladder Cancer With Remote Iridium-192 Afterloading", 21 Eur Urol 1992, 245-249 (1992).

Chun, M. etal. "Interstitial Iridium-192 Implantation for Malignant Brain Tumours. Part II: Clinical Experience," *The British Journal of Radiology*, vol. 62, 158-62 (1989).

Garfield, J. et al., "Postoperative Intracavitary Chemotherapy of Malignant Gliomas," *J. Neurosurg.*, vol. 39, 315-22 (Sep. 1973).

Gutin, P. et al., "Brachytherapy of Recurrent Malignant Brain Tumors With Removable High-Activity Iodine-125 Sources," *J. Neurosurg.*, vol. 60, 61-8 (1984).

Johannesen, T.B. et al., "Intracavity Fractionated Balloon Brachytherapy in Glioblastoma," *Acta Neurochir (Wien)*, vol. 141, 127-33 (1999).

Leibel, S. et al., "The Integration of Interstitial Implantation Into the Preliminary Management of Patients With Malignant Gliomas: Results of a Phase II Northern California Oncology Group Trial," *Am. J. Clin. Oncol. (CCT)*, vol. 10, No. 2, p. 106 (1987).

Roberts, D. et al., "Interstitial Hyperthermia and Iridium Brachytherapy in Treatment of Malignant Glioma," *J. Neurosurg.*, vol. 64, 581-7 (1986).

Wu, A. et al., "Interstitial Iridium-192 Implantation for Malignant Brain Tumours, Part 1: Techniques of Dosimetry Planning," *The British Journal of Radiology*, vol. 62, 154-7 (1989).

* cited by examiner

BRACHYTHERAPY APPARATUS AND METHOD FOR TREATING A TARGET TISSUE THROUGH AN EXTERNAL SURFACE OF THE TISSUE

BACKGROUND OF THE INVENTION

The present invention relates generally to apparatus and methods for use in treating proliferative tissue disorders, and more particularly to apparatus and methods for the treatment of such disorders in the body by the application of radiation to a tissue surface.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radiation source inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance of normal tissue. In brachytherapy, radiation doses are highest in close proximity to the radiotherapeutic source, providing a high tumor dose while sparing surrounding normal tissue.

One example of a brachytherapy device is disclosed in U.S. Pat. No. 5,030,195 of Nardi, entitled "Radioactive Seed Patch for Prophylactic Therapy." Nardi describes a method and apparatus for treating tissue surrounding a surgically excised tumor with radioactive emissions to kill any cancer cells that may be present in the tissue surrounding the excised tumor. In order to implement the radioactive emissions, Nardi provides a low-energy, nonabsorbable radioactive seed patch made from a plastic mesh having Iodine-125 seeds threaded therein. The patch is put in place during the time of surgery after the resection of the tumor, and remains therein indefinitely.

While the apparatus described in Nardi provides some advantages, the patch is limited to use with permanently implanted radioactive seeds, which in some applications can be less effective than other radiation sources. Moreover, Nardi does not disclose methods for tailoring the radiation dosage to avoid fully dosing sensitive tissue or to reduce the amount of radiation that escapes into the body.

Accordingly, there is still a need for a device that can be used to effectively deliver radiation from a solid and/or liquid radioactive source to target tissue within the human body.

SUMMARY OF THE INVENTION

The present invention generally provides a brachytherapy device for treating target tissue surrounding a surgical extraction site. In one embodiment the device includes an insertion member having a proximal portion, a distal portion, and at least one lumen extending therethrough. A fluid retaining member is mated to the distal portion of the insertion member and has a first surface shaped to conform to a predetermined external surface area of a tissue to be treated, and at least one cavity formed therein in fluid communication with the at least one lumen in the insertion member. A plurality of anchor members can be distributed about a periphery of the first surface to anchor the first surface to an external surface area of a tissue to be treated.

In use, the brachytherapy device is adapted to receive a radiation source through the at least one lumen into a cavity in the fluid retaining member for delivering radiation to the tissue to be treated. Preferably, the fluid retaining member is shaped to provide a uniform radiation dosage throughout the first surface when the fluid retaining member is filled with a radioactive fluid. The fluid retaining member can also include a second surface opposed to the first surface, and a peripheral wall extending between the first and second surfaces to define the cavity therein. The peripheral wall preferably has a substantially uniform depth. In an exemplary embodiment, the fluid retaining member can be substantially disk-shaped or oval-shaped.

In another embodiment, the fluid retaining member can be movable between a closed position in which the fluid retaining member is disposed adjacent the insertion member, and an open position in which the fluid retaining member extends outward from the insertion member. Preferably, the fluid retaining member is an expandable balloon member that is inflated in the open position and deflated in the closed position. The expandable balloon member can have a predetermined shape in the open position such that, when inflated, the expandable balloon member is effective to cover a predetermined area of tissue. While the predetermined shape can vary, in an exemplary embodiment the predetermined shape of the expandable balloon member is substantially disk-shaped or oval-shaped. In yet another embodiment, the fluid retaining member can be formed of a shape memory material, and can have a three-dimensional shape in the open position, and a substantially folded shape in the closed position. Again, the fluid retaining member is preferably substantially disk-shaped or oval-shaped in the open position.

In other aspects of the present invention, a brachytherapy device is provided having an elongate catheter member with a proximal portion, a distal portion, and at least one lumen extending therethrough. A balloon member is disposed around the distal portion of the elongate catheter member and has a cavity formed therein and in fluid communication with at least one lumen in the elongate catheter. The balloon member includes a first tissue contacting surface shaped to conform to a predetermined external surface area of a tissue to be treated. The device further includes a radiation source in the form of a liquid disposed within the cavity of the balloon.

The catheter member can be mated with the balloon member at any position on the balloon. Exemplary sites for connecting the catheter member and the balloon member include the balloon treatment surface, a surface opposite the treatment surface and the periphery of the balloon member.

In yet another embodiment of the present invention, a method for treating tissue surrounding a surgical extraction site is provided. The method includes the step of providing at least one brachytherapy apparatus for delivering radioactive emissions. The apparatus preferably includes a catheter member having proximal and distal ends and at least one lumen extending therethrough, and at least one fluid retaining member disposed proximate to the distal end of the catheter member. The fluid retaining member includes a cavity formed therein in communication with the at least one lumen in the catheter member, and a first surface shaped to conform to a predetermined external surface area of a tissue to be treated. The method further includes the steps of intraoperatively placing the at least one brachytherapy apparatus on an external tissue surface of a tissue to be treated, and introducing a controlled dose of a radiation source through the at least one lumen in the catheter to the fluid retaining member to treat tissue. Preferably, the radiation source is placed into the brachytherapy apparatus after placement of the apparatus on a tissue surface, and is removed from the apparatus before removal of the apparatus. The method can also include the step of attaching the fluid retaining member to the predetermined external surface area of a tissue to be treated.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DETAILED DESCRIPTION OF THE INVENTION

Figure 1:
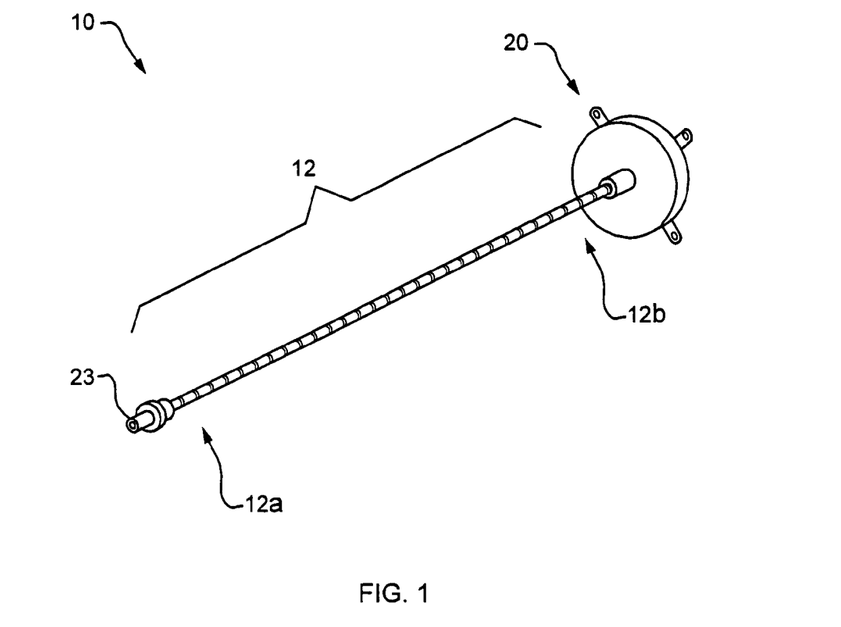
FIG. 1 is perspective view illustration of one embodiment of a brachytherapy device according to the present invention.
Figure 2:
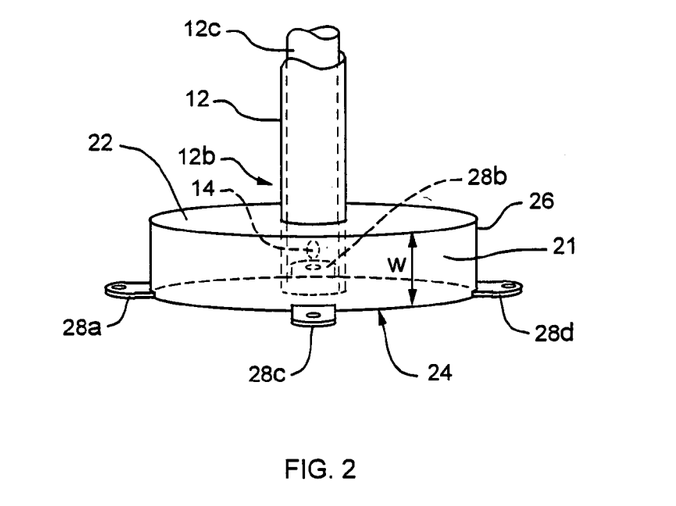
FIG. 2 is a side view illustration of the distal portion of the device shown in FIG. 1.

The present invention generally provides a radiotherapy device, and preferably a brachytherapy device, for delivering radiation to tissue and/or bone. While the system can be used for a variety of purposes, the system is preferably used to treat tissue proximate to a resected tumor site, and more particularly, to treat an external surface of tissue surrounding a closed tumor resection site, for example, in a patient's lungs. FIGS. 1 and 2 illustrate one embodiment of a brachytherapy device 10 which generally includes an insertion member, e.g., a catheter member 12, having a proximal portion 12a, a distal portion 12b, and at least one lumen 12c extending therethrough. An expandable surface element, illustrated as fluid retaining member 20, can be mated to the distal portion 12b of the catheter member 12 and includes a cavity 21 formed therein in fluid communication with at least one lumen 12c in the catheter member 12. In use, the fluid retaining member 20 is disposed on an external surface area of a tissue to be treated, and the cavity 21 is effective to receive a radiation source, typically either in liquid or solid form, for delivering radiation to the tissue to be treated.

The catheter member 12 can have a variety of configurations, but is preferably a semi-flexible or flexible elongate member having a proximal portion 12a, a distal portion 12b, and at least one lumen 12c formed therein that extends through the proximal and distal portions 12a, 12b. The lumen 12c can terminate at or near a distal port 14 formed in the distal portion 12b of the catheter 12. As shown in FIG. 1, the proximal end 12a of the catheter 12 preferably includes a percutaneous port 23 for providing access to the fluid retaining member 20 once the device 10 is implanted in a patient. While only one inner lumen 12c is illustrated in FIG. 2, a person skilled in the art will readily appreciate that the catheter member 12 can have one or more inner lumens, or that other means known in the art can be used to deliver fluid and/or air to the fluid retaining member 20.

The fluid retaining member 20 can have a variety of configurations, shapes, and sizes. However, the fluid retaining member preferable includes a cavity 21, formed therein in fluid communication with at least one lumen 12c formed in the catheter member 12. In one embodiment, the fluid retaining member 20 is configured and adapted for receiving a fluid radiation source. Moreover, at least one outer surface of the fluid retaining member 20 is preferably a tissue-contacting surface that is adapted to be positioned on, and optionally conform to, a predetermined external surface area of a tissue to be treated. In addition, a person skilled in the art will appreciate that the fluid retaining member can include any number of cavities formed therein, and one or more surfaces can be adapted to be positioned on an external tissue surface to be treated.

As shown in FIG. 2, the fluid retaining member 20 includes a first, tissue contacting surface 24, a second, opposed surface 22, and a peripheral sidewall 26 extending therebetween. The first and second surfaces 24, 22 can each have virtually any size, but preferably the first surface 24 has a size that is sufficient to cover a predetermined external surface area of a tissue to be treated. The shape of the first and second surfaces 24, 22 can also vary, but the first surface 24 should be adapted to be positioned on an external tissue surface. In an exemplary embodiment, the first surface 24 is substantially planar, but is preferably flexible or semi-flexible to allow the surface 24 to conform to the tissue surface. The second surface 22 can also vary in shape and size, but preferably has a shape and size substantially the same as the first surface 22 to provide for uniform radiation dosage where a liquid radioisotope within fluid retaining member 20 provides the radiation dose. In one embodiment, uniform radiation dosage can be achieved by providing a peripheral sidewall 26 having a substantially constant width w extending between the first and second surfaces 24, 22. The uniform width w of the sidewall 26 facilitates the even distribution of radioactive fluid within the fluid retaining member 20, thereby providing a uniform radiation dosage, with the exception of edge effects, throughout the first surface 24 when the fluid retaining member is filled with a radioactive fluid.

While the embodiment of FIGS. 1 and 2 illustrates a substantially disk-shaped fluid retaining member 20, which is advantageous because it can provide a substantially uniform radiation dosage, a person skilled in the art will appreciate that the fluid retaining member 20 can have a variety of configurations. By way of non-limiting example, the first and second opposed surfaces of the fluid retaining member can be square, oval, rectangular, etc. In one preferred embodiment, the first surface is oval in shape. The inventors have discovered that an oval shape can provide complete coverage of a target tissue region while being easier to manipulate, in particular during surgery for treatment of lung tumors, than other shapes. Moreover, while the size of the fluid retaining member 20 can be predetermined, the size can be selectable during treatment by inflating the fluid retaining member to a desired level. In certain embodiments of the invention, the surface area of the first surface can be between about 4 cm$^2$ to 100 cm$^2$.

The fluid retaining member 20 also preferably includes at least one anchor member 28a-d formed thereon or mated thereto for attaching the fluid retaining member 20 to the tissue surface. The anchor members 28a-d can be formed on or mated to any portion of the fluid retaining member 20, and can have a variety of configurations. Preferably, each anchor member 28a-d is disposed around a periphery of the first surface 22. In the illustrated embodiment, such a configuration results in anchor members 28a-d being placed around the peripheral wall 26 of, or adjacent to, the first surface 24. A variety of anchor members 28a-d can be used including, for example, eyelets, hooks, adhesives, and combinations thereof. FIG. 2 illustrates anchor members 28a-d in the form of eyelets. In use, each anchor member 28a-d can be sutured or otherwise attached to the tissue surface to securely implant the fluid retaining member 20 within the patient.

In the embodiment illustrated in FIGS. 1 and 2, catheter 12 is attached to fluid retaining member 20 at second surface 22, and possibly also at first surface 24. In a further embodiment, illustrated in FIG. 3, catheter 12 is attached to fluid retaining member 20 at one portion, and preferably at two opposed portions, of side wall 26. By attaching catheter 12 along sidewall 26, a device 10 geometry is obtained that is preferred for insertion of the device to a desired treatment area in certain treatment procedures. For example, the geometry of the embodiment illustrated in FIG. 3 can be preferred for use in treating lung tumors where device 10 must be moved laterally beneath a patient's ribs. While in the embodiment illustrated in FIG. 3 the catheter 12 is centrally connected to fluid retaining member 20, a person skilled in the art will recognize that other configurations are possible.

The fluid retaining member 20 can also include a variety of other features not shown or described herein. In another embodiment, the fluid retaining member 20 can be adapted to shield radiation-sensitive tissue. By way of non-limiting example, all or a portion of the second surface 22 and/or the peripheral wall 26 can be formed from, or coated with, a radio-opaque material that is effective to shield tissue surrounding the treatment site. In an exemplary embodiment, the entire fluid-retaining member 20, except the tissue contacting surface 24, is radio-opaque. The coating (not shown) can be strategically positioned to shield radiation sensitive tissue, and/or to provide an asymmetric isodose curve as described in U.S. Pat. No. 6,482,142, issued on Nov. 19, 2002, and entitled "Asymmetric Radiation Dosing Apparatus and Method," which is incorporated herein by reference.

Radio-opaque materials suitable for coating include, for example, barium, tungsten, bismuth, tantalum, and tin. As an alternative to coating portions of the fluid retaining member 20, a radiation-blocking or absorbing shield (not shown) can be positioned between within or around particular areas of the fluid retaining member 20 to produce a desired isodose curve. A person skilled in the art will appreciate that other configurations may be employed to achieve the desired isodose curves and/or shielding of radiation sensitive tissue.

Figure 4A:
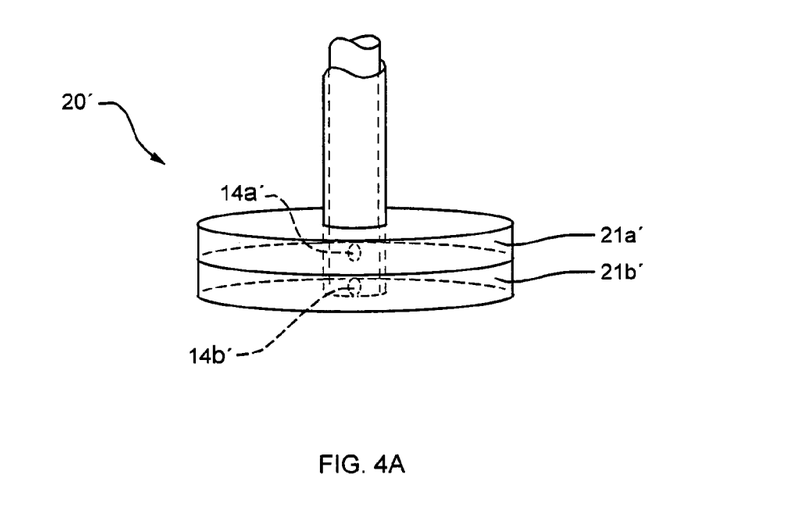
FIG. 4A is an illustration of another embodiment of the brachytherapy device containing multiple cavities.
Figure 4B:
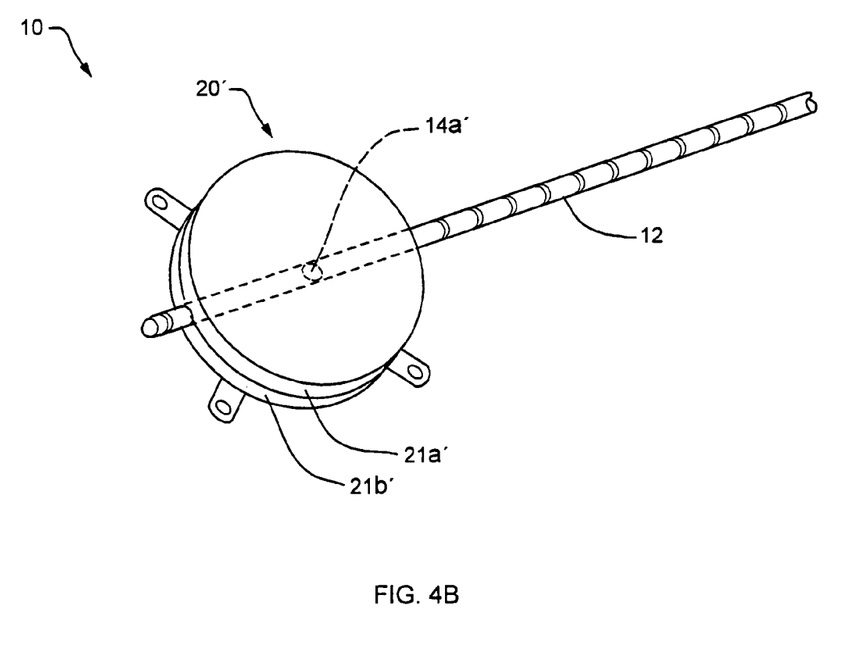
FIG. 4B is an illustration of another embodiment of the brachytherapy device containing multiple cavities.

In yet another embodiment, the fluid retaining member can be adapted to provide spacing between the radiation source and the tissue. By way of non-limiting example, as shown in FIGS. 4A and 4B, the fluid retaining member 20' can include a divider disposed therein to separate the inner cavity into first and second cavities 21a', 21b'. Each cavity 21a', 21b' is preferably in communication with a port 14a', 14b' to allow a radiation source to be delivered to the first cavity 21a', and fluid or air to be delivered to the second cavity 21b'. In use, the second cavity 21b' is effective to space the radiation source a distance apart from the tissue surface. By providing a uniform spacing between the radiation source (in the illustrated embodiment, a fluid radiation source would be preferred, such as Iotrex®, Cytyc Corporation, Marlborough, Mass.), a uniform prescribed radiation dose can penetrate into the target tissue while minimizing the chance of necrosis of healthy tissue in contact with or proximate to fluid retaining member 20' as described in U.S. Pat. No. 6,413,204 to Winkler et at, which is incorporated herein by reference in its entirety. A person skilled in the art will appreciate that a variety of techniques can be used to provide spacing between the radiation source and the tissue. By way of non limiting example, the fluid retaining member 20' can include a second balloon member disposed around the fluid retaining member for providing spacing, as described in U.S. Pat. No. 6,413,204.

In addition to providing spacing, a second inner cavity can be used to deliver a therapeutic agent to the target tissue. For example, at least a portion of retaining member 20 can be defined by a porous material, and can be used to deliver a therapeutic agent from cavity 21b' to adjacent tissue. In one embodiment, tissue contacting surface 24 is defined by a porous membrane through which a therapeutic agent can be delivered. U.S. Pat. No. 6,083,148 to Williams discloses exemplary brachytherapy methods and apparatus using porous balloon walls, and is incorporated herein by reference in its entirety. The therapeutic agent is preferably a medically useful agent, for example a chemotherapy agent, an anti-neoplastic agent, an anti-angiogenesis agent, an immuno-modulator, a hormonal agent (including agonists and antagonists), an immunotherapeutic agent, an antibiotic, or combinations thereof. Other therapeutic agents and useful porous materials are disclosed in U.S. Pat. No. 6,200,257 to Winkler which is incorporated herein by reference in its entirety.

Figure 3:
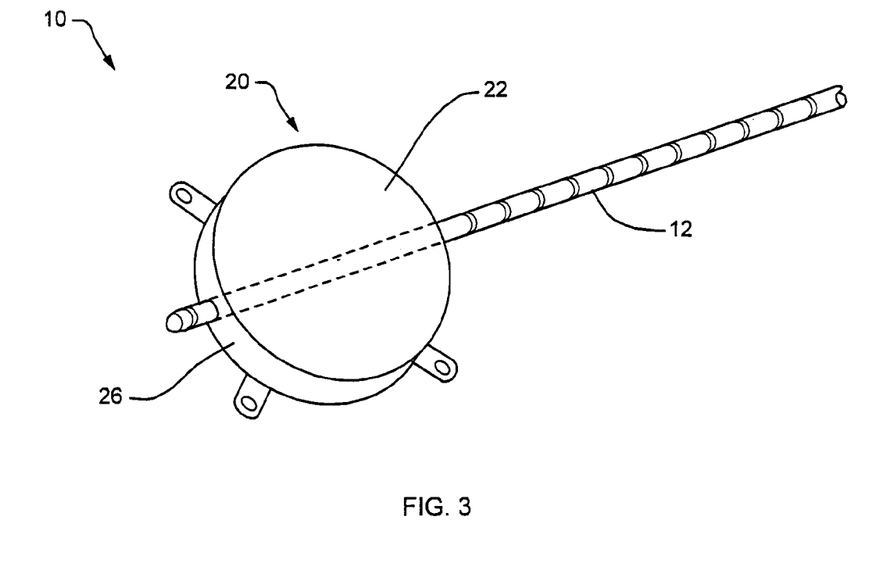
FIG. 3 is an illustration of another embodiment of the brachytherapy device of the present invention shown in a perspective view.

In use, the fluid retaining member 20 is preferably movable between a closed, unexpanded form, and an open, expanded form in which the fluid retaining member 20 has a predetermined shape, as shown in FIGS. 1, 2 and 3. When positioned in the expanded form, the predetermined shape is preferably adapted to cover an external surface area of a target tissue to be dosed with radiation. Movement of the fluid retaining member 20 between the open and closed positions can be accomplished by a variety of techniques. While the fluid retaining member 20 is preferably inflated using liquid, air, or a radiation source, movement can optionally be accomplished using an actuating member (not shown), such as a wire, pulley assembly, lever, or similar device, effective to move the fluid retaining member to one of the open or closed positions. A person skilled in the art will readily appreciate that a variety of different actuating members can be used to position the fluid retaining member 20 within the patient adjacent the extraction site, and to move the fluid retaining member 20 between the open and closed positions.

In an exemplary embodiment, the fluid retaining member 20 is an expandable balloon member having a predetermined shape in the expanded position. It will be understood that the term "balloon" is intended to include distensible devices which can be, but need not be, constructed of an elastic material. In an alternative embodiment, the fluid retaining member 20 can be formed from a shape memory material, wherein the fluid retaining member 20 has a three-dimensional shape in the open position, and a substantially folded shape in the closed position.

With no limitation intended, the fluid retaining member 20 can be formed from a polymeric film wall, which may comprise a biocompatible, radiation resistant polymer. Suitable polymers include, for example, silastic rubbers, polyurethanes, polyethylene, polypropylene, polyester, and PVC. Still further, the fluid retaining member 20 can be formed according to the balloon and/or expandable surface elements described in U.S. Pat. No. 6,413,204, which is incorporated herein by reference in its entirety.

Figure 5A:
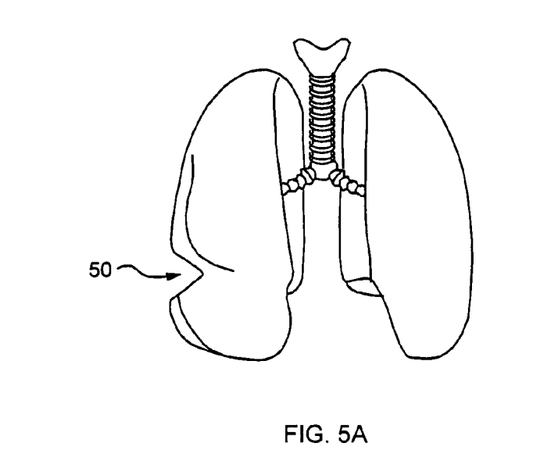
FIG. 5A is an illustration of a patient's lung having a lesion surgical resected therefrom.
Figure 5B:
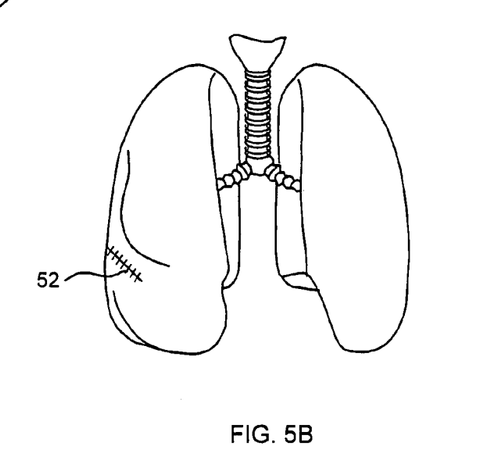
FIG. 5B is an illustration of the lung shown in FIG. 5A having the resected lesion that is closed by sutures.
Figure 5C:
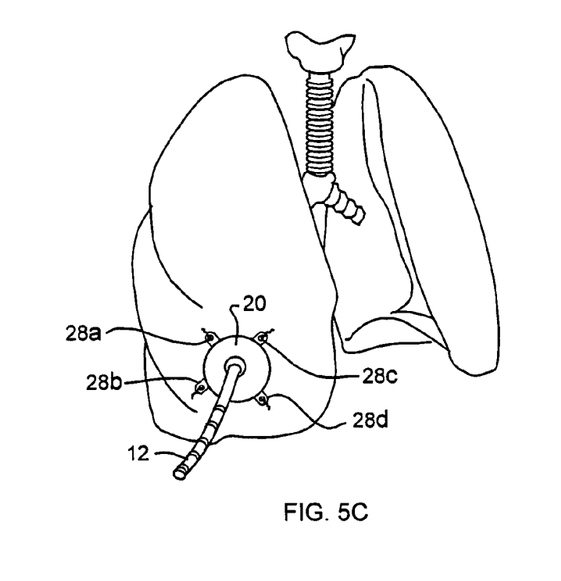
FIG. 5C is an illustration of the lung shown in FIG. 5B having a brachytherapy device according to the present invention attached thereto.

The present invention also provides a method for treating a target tissue through an external surface area of the target tissue. FIGS. 5A-5C illustrate one embodiment of a method for using a brachytherapy device to treat a resected lung tumor by application of a brachytherapy device to an external surface of the lung. In FIG. 5A, the cancerous tissue has been resected from the lung creating a resected cavity or "wedge" 50. After wedge resection, the cavity 50 is sutured or stapled closed, as shown in FIG. 5B, which illustrates sutures 52. A brachytherapy device according to the present invention can then be intra-operatively placed into the patient's body and the fluid retaining member 20 can be positioned over an external surface of the lung proximate to the sutured resection site 52 (a predetermined external surface area). If the fluid retaining member 20 is introduced in a closed configuration, the fluid retaining member 20 can be inflated or otherwise moved to the open position, at which point it is preferably attached to the tissue using one or more of the anchor members 28a-d. Inflation can be achieved with air or other fluids, such as saline or a radiation absorbing fluid such as a contrast media used in angiography, or alternatively the radioactive fluid can be pre-loaded into the fluid retaining member prior to anchoring the fluid retaining member to the tissue. Preferably, however, the radioactive fluid is introduced into the fluid retaining member 20 after it is anchored to the tissue surface. The radioactive source dwells in the fluid retaining member 20 until the prescribed dose of radiotherapy is delivered, or the radioactive source can be inserted for prescribed amounts of time on a daily or other scheduled basis until the prescribed dosage has been achieved. The radioactive source is then retrieved and the catheter 12 is removed.

The application of radiotherapy using a radioactive source can also be performed according to the many descriptions and examples provided in U.S. Pat. No. 6,413,204, issued Jul. 2, 2002, and entitled "Interstitial Brachytherapy Apparatus and Method for Treatment of Proliferative Tissue Diseases," which has been incorporated herein by reference above. The radiation treatment may end upon removal of the brachytherapy apparatus, or the brachytherapy may be supplemented by further doses of radiation supplied externally. By way of non-limiting example, the radioactive material can be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel. One radioactive material useful in the invention is Iotrex™, a sterile single use, non-pyrogenic solution containing sodium 3-($^{125}$I)iodo-4-hydroxybenzenesulfonate ($^{125}$I-HBS), available from Proxima Therapeutics, Inc. of Alpharetta, Ga.

In addition, the radiation source employed in the brachytherapy device and method of the invention can be solid or another non-liquid radiation source such as an x-ray emitter. Again, by way of non-limiting example, a solid radiation source for use with the invention could include radioactive micro spheres of the type available from the 3M Company of St. Paul, Minn. This radioactive source can either be pre-loaded into the catheter at the time of manufacture or loaded into the device after it has been implanted. The solid radiation emitting material can be inserted through catheter 12 on a wire, for example, using an afterloader (not shown). Such a solid radioactive core configuration offers an advantage in that it allows a wider range of radionuclides than if one is limited to liquids. Such radionuclides that could be used with the delivery device of the present invention are currently generally available as brachytherapy radiation sources. In this embodiment, a solid spherical radiation source is surrounded by fluid retaining member 20, defining a spatial volume between the radiation source and the fluid retaining member that can be occupied by a radioactive ray absorbing material, such as air, water, or a contrast material.

In a further embodiment, the radiation source, instead of comprising a single solid sphere, may comprise a plurality of radiation emitting particles 44 strategically placed within the fluid retaining member 20 so as to radiate all directions, or more particularly toward the target tissue through the tissue contacting surface 24, with a substantially equal intensity. This plurality of radiation emitting particles can be mounted on the distal end of a plurality of wires that are routed through the catheter body 12 and exit a plurality of ports formed through the wall of the catheter body. This arrangement allows the exact positioning of the individual radiation sources so as to generate a desired resultant profile.

A person having skilled in the art will appreciate that the foregoing is only illustrative of the principles of the invention, and that various modifications can be made by those skilled in the art without departing from the scope and spirit of the invention. All references cited herein are expressly incorporated by reference in their entirety.

What is claimed is:

1. A brachytherapy device, comprising:
an elongate catheter member having a proximal portion, a distal portion, and at least one lumen extending therethrough;
a balloon member disposed around the distal portion of the elongate catheter member and having a cavity formed therein and in fluid communication with at least one lumen in the elongate catheter, the balloon member having a first tissue contacting surface shaped to conform to a predetermined external surface area of a tissue to be treated; and
a radiation source in the form of a liquid disposed within the cavity of the balloon;
wherein the balloon member includes a plurality of anchor members distributed about a periphery of the first surface to anchor the first surface to an external surface area of the tissue to be treated; and
wherein the balloon member includes a second surface opposed to the first surface, and a peripheral wall extending between the first and second surfaces to define the cavity therein.

2. The device of claim 1, wherein the peripheral wall has a substantially uniform depth.

3. The device of claim 1, wherein the balloon member is substantially disk-shaped.

4. The device of claim 1, wherein at least a portion of at least one of the second surface and the peripheral wall are radio-opaque to protect non-targeted tissue from radiation.

5. The device of claim 1, wherein the balloon member is movable between a closed, deflated position in which the balloon member is disposed adjacent the insertion member, and an open, inflated position in which the balloon member extends outward from the insertion member; and wherein the balloon member has a predetermined shape in the open position such that, when inflated, the balloon member is effective to cover a predetermined area of tissue; and wherein the predetermined shape of the balloon member is substantially disk-shaped.

6. A method for treating a target tissue through an external surface area of the target tissue, comprising:

providing at least one brachytherapy apparatus for delivering radioactive emissions, the apparatus having a catheter member having proximal and distal ends and at least one lumen extending therethrough, at least one fluid retaining member disposed proximate to the distal end of the catheter member, the fluid retaining member including a cavity formed therein in communication with the at least one lumen in the catheter member, a first surface shaped to conform to a predetermined external surface area of a tissue to be treated, and a plurality of anchor members distributed about a periphery of the first surface to anchor the first surface to an external surface area of a tissue to be treated;

intraoperatively placing the at least one brachytherapy apparatus on an external tissue surface of a tissue to be treated; and introducing a controlled dose of a radiation source through the at least one lumen in the catheter to the fluid retaining member to treat tissue;

wherein the fluid retaining member is movable between a closed position in which the fluid retaining member is disposed adjacent the catheter member, and an open position in which the fluid retaining member extends outward from the catheter member; and wherein the fluid retaining member is an expandable balloon member that is inflated in the open position and deflated in the closed position; and wherein the expandable balloon member has a predetermined shape in the open position such that, when inflated, the balloon member is effective to cover the predetermined external surface of a tissue to be treated; and wherein the predetermined shape of the balloon member is substantially disk-shaped.

7. The method of claim 6, wherein the fluid retaining member is formed of a shape memory material, and wherein the fluid retaining member has a three-dimensional shape in the open position, and a substantially folded shape in the closed position; and wherein the fluid retaining member is substantially disk-shaped in the open position.

* * * * *